(12) United States Patent
Hsu et al.

(10) Patent No.: US 11,320,468 B2
(45) Date of Patent: May 3, 2022

(54) WIDE DYNAMIC RANGE CURRENT MEASUREMENT FRONT-END

(71) Applicant: The Regents of the University of California, Oakland, CA (US)

(72) Inventors: Chung-Lun Hsu, Walnut, CA (US); Drew A. Hall, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 133 days.

(21) Appl. No.: 16/649,046

(22) PCT Filed: Sep. 19, 2018

(86) PCT No.: PCT/US2018/051820
§ 371 (c)(1),
(2) Date: Mar. 19, 2020

(87) PCT Pub. No.: WO2019/060461
PCT Pub. Date: Mar. 28, 2019

(65) Prior Publication Data
US 2020/0292594 A1    Sep. 17, 2020

Related U.S. Application Data

(60) Provisional application No. 62/560,634, filed on Sep. 19, 2017.

(51) Int. Cl.
*H03M 1/10* (2006.01)
*G01R 19/255* (2006.01)
(Continued)

(52) U.S. Cl.
CPC ......... *G01R 19/255* (2013.01); *G01N 33/483* (2013.01); *H03M 1/12* (2013.01);
(Continued)

(58) Field of Classification Search
CPC ..... G01R 19/255; G01N 33/483; H03M 1/12; H03M 3/458; H03F 2203/45631;
(Continued)

(56) References Cited

U.S. PATENT DOCUMENTS 3,678,500 A    7/1972  Bauer
3,710,374 A    1/1973  Kelly
(Continued)

*Primary Examiner* — Joseph J Lauture
(74) *Attorney, Agent, or Firm* — Perkins Coie LLP

(57) ABSTRACT

In one aspect, an analog-to-digital converter circuit includes a transimpedance amplifier including a feedback capacitor electrically connected between an inverting or a non-inverting input of the transimpedance amplifier and an output of the transimpedance amplifier. The circuit includes an hourglass switch electrically connected on a first side to a first input and a second input, and electrically connected on a second side to the non-inverting input and the inverting input. A fine input current to the transimpedance amplifier is received at the first and second inputs. In a first mode, the hourglass switch electrically connects the first input to the non-inverting input and the second input to the inverting input, and in a second mode, the hourglass switch electrically connects the second input to the non-inverting input and the first input to the inverting input.

28 Claims, 14 Drawing Sheets

(51) Int. Cl.
     *G01N 33/483*     (2006.01)
     *H03M 1/12*     (2006.01)
     *H03M 3/00*     (2006.01)
     *H03F 1/26*     (2006.01)
     *H03F 1/02*     (2006.01)

(52) U.S. Cl.
     CPC ........... *H03M 3/458* (2013.01); *H03F 1/0205* (2013.01); *H03F 1/26* (2013.01); *H03F 2203/45116* (2013.01); *H03F 2203/45631* (2013.01)

(58) Field of Classification Search
     CPC ............. H03F 2203/45116; H03F 1/26; H03F 1/0205; H03F 3/217
     See application file for complete search history.

(56) References Cited

U.S. PATENT DOCUMENTS

| | | |
|---|---|---|
| 2009/0273366 A1 | 11/2009 | Korobeynikov et al. |
| 2013/0331052 A1 | 12/2013 | Jensen et al. |
| 2017/0047896 A1* | 2/2017 | Shu ....................... H03F 1/0205 |

* cited by examiner

1200

1210 — Integrating, by a transimpedance amplifier including a feedback capacitor, a fine input current, wherein the transimpedance amplifier has a non-inverting input and an inverting input 1220 — Selecting a polarity of the fine input current by switching between a first mode, wherein a first input is connected to a non-inverting input to the transimpedance and a second input is connected to an inverting input to the transimpedance amplifier, or a second mode, wherein the first input is connected to the inverting input to the transimpedance and the second input is connected to the non-inverting input to the transimpedance amplifier, wherein an hourglass switch asynchronously selects the mode to be the first mode or the second mode to prevent the feedback capacitor from saturating 1230 — Removing a coarse current from an input current to the transimpedance amplifier, wherein the input current is equal to the fine input current added to the coarse current, wherein the coarse current removed from the input current reduces a range of the fine current and improves a linearity between the analog input voltage and the digital binary value

*FIG. 12*

WIDE DYNAMIC RANGE CURRENT MEASUREMENT FRONT-END

CROSS REFERENCE TO RELATED APPLICATION

This patent document is a 371 National Phase Application of International Application No. PCT/US2018/051820, filed on Sep. 19, 2018, which claims the benefit of priority of U.S. Provisional Patent Application No. 62/560,634, filed on Sep. 19, 2017. The entire contents of the before-mentioned patent applications are incorporated by reference as part of the disclosure of this document.

TECHNICAL FIELD

The present disclosure relates to circuits for electronic measurement of small currents.

BACKGROUND

Scientific, industrial, biological, and other sensors may produce electrical currents that are indicative of the feature being sensed. Determining the value of the current from the sensor or other device can be important to the parameter(s) measured. New methods and techniques are needed for measuring currents from sensors, particularly for small electrical currents.

SUMMARY

Apparatuses, methods, and systems are disclosed. In one aspect, an analog-to-digital converter circuit is disclosed. The circuit includes a transimpedance amplifier including a feedback capacitor, wherein the transimpedance amplifier has a non-inverting input and an inverting input. The capacitor is electrically connected between the inverting or non-inverting input and an output of the transimpedance amplifier. The circuit includes an hourglass switch electrically connected on a first side to a first input and a second input, and electrically connected on a second side to the non-inverting input and the inverting input, wherein in a first mode the hourglass switch electrically connects the first input to the non-inverting input and the second input to the inverting input, wherein in a second mode, the hourglass switch electrically connects the second input to the non-inverting input and the first input to the inverting input. A fine input current to the transimpedance amplifier is received at the first and second inputs.

The circuit may further include the following features in various combinations. The circuit may further include a linear digital-to-analog converter electrically connected to the first and second inputs, wherein the linear digital-to-analog converter generates a coarse current to remove from an input current leaving the fine input current as input current to the transimpedance amplifier at the first and second inputs. The linear digital-to-analog converter may generate a coarse current to remove from an input current leaving the fine current as input current to at the first and second inputs, wherein the coarse current removed from the input current reduces a range of the fine current causing an improved linearity of the analog-to-digital converter circuit. The hourglass may switch asynchronously to select the first mode or the second mode to prevent the feedback capacitor from saturating. The analog-to-digital converter may further include a comparator electrically connected to an output of the transimpedance amplifier and a reference voltage, wherein when the output exceeds the reference voltage the comparator generates a pulse, and wherein the pulse causes the hourglass switch to switch from the first mode to the second mode or the second mode to the first mode. The circuit may further include a pulse counter to electrically connected to the comparator to count pulses from the comparator including the pulse, wherein the pulse counter is representative of the fine input current. The hourglass switch may be a cross-point switch or a cross-bar switch. The linear digital-to-analog converter may include a first order predictor, a dynamic element matching circuit, and a binary-weighted digital-to-analog converter. The first order predictor may estimate the input current for a next oversampling cycle and controls the binary-weighted digital-to-analog converter to generate the coarse current to be removed from the input current leaving the fine current as the first and second inputs to the hourglass switch. The circuit may further include one or more sensors including one or more of a nanotube sensor, a patch-clamp sensor, an electrochemical sensor, or a nanopore sensor, wherein the one or more sensors provide the input current. The input current may be in a range between 100 femtoamps and 10 microamps. The hourglass switch and the linear analog to digital converter may cause the analog-to-digital converter circuit to have a dynamic range of 160 dB or more. The hourglass switch and the linear analog to digital converter may cause the analog-to-digital converter circuit to have a Schreier figure of merit equal to or greater than 197 dB.

In another aspect, a method of representing an analog voltage by a digital binary value is disclosed. The method includes integrating, by a transimpedance amplifier including a feedback capacitor, a fine input current, wherein the transimpedance amplifier has a non-inverting input and an inverting input. The method further includes selecting a polarity of the fine input current by switching between selecting a first mode, wherein a first input to be connected to a non-inverting input to the transimpedance and a second input to be connected to an inverting input to the transimpedance amplifier, or a second mode, wherein selecting the first input to be connected to the inverting input to the transimpedance and the second input to be connected to the non-inverting input to the transimpedance amplifier, wherein an hourglass switch is selected asynchronously to be in the first mode or the second mode to prevent the feedback capacitor from saturating. The method further includes removing a coarse current from an input current to the transimpedance amplifier, wherein the input current is equal to the fine input current added to the coarse current, wherein the coarse current removed from the input current reduces a range of the fine current improves a linearity of a relationship between the analog input voltage and the digital binary value. The method may further include comparing, by a comparator, an output of the transimpedance amplifier to a reference voltage, wherein when the output exceeds the reference voltage the comparator generates a pulse, and wherein the pulse causes the hourglass switch to switch from the first mode to the second mode or the second mode to the first mode. The method may further include counting pulses from the comparator including the pulse, wherein a count of the pulses is representative of the fine input current.

In yet another aspect, a circuit is disclosed that includes a transimpedance amplifier including a feedback capacitor, wherein the transimpedance amplifier has a non-inverting input and an inverting input, and/or an hourglass switch connected on a first side to a first input and a second input, and connected on a second side to the non-inverting input and the inverting input. The capacitor may be electrically connected between the inverting or non-inverting input and an output of the transimpedance amplifier. The circuit may further include a linear digital-to-analog converter connected to the first and second inputs, wherein an input current is received at the first and second inputs.

BRIEF DESCRIPTION OF THE DRAWINGS

FIG. 12 depicts an example of a process, in accordance with some example embodiments.

DETAILED DESCRIPTION

Current measurement is used in many biosensing applications, such as the detection of neurotransmitters and the monitoring of intercellular molecular dynamics. The measured current may be very small. For example, single molecule biosensors produce sub-picoamp (µA) signal currents that may be superimposed on a slowly varying nanoamp (nA) to microamp (µA) background current, as is the case with some nanopores. As such, the readout circuitry may have a wide dynamic range (>120 dB), high linearity (>14 bits), and may have a low bandwidth (e.g., a few Hz to kHz).

The subject matter disclosed herein includes an analog-to-digital converter (ADC) which may be referred to as an "hourglass ADC." The hourglass ADC includes an hourglass switch and a first-order predictor each of which improves the linearity of the hourglass ADC over conventional ADCs. The hourglass switch prevents a feedback capacitor ($C_F$) in a transimpedance amplifier from saturating thereby improving linearity of the hourglass ADC. The first order predictor improves the linearity of a binary-weighted digital-to-analog converter (DAC) used to reduce the input current to the transimpedance amplifier. For example, an input current may be split between $i_{fine}$ and $i_{coarse}$ (see, for example, FIG. 1). The first order predictor extracts the $i_{coarse}$ current leaving $i_{fine}$ as the current into the transimpedance amplifier. By extracting $i_{coarse}$, the transimpedance amplifier has a smaller range of current to process thereby improving the linearity and ensuring the feedback capacitor, $C_F$, does not saturate. By removing $i_{coarse}$, the overall linearity of the hourglass ADC is improved.

In one aspect, a current measurement front-end using a modified asynchronous $\Delta\Sigma$ (delta-sigma) modulator is disclosed. Some example embodiments may include 1) a continuous time, oscillator-based hourglass ADC that asynchronously folds the input signal within the supply, 2) noise shaping to suppress quantization noise, and 3) digital linearity correction that relaxes the amplifier bandwidth requirement thereby reducing power consumption. Some example embodiments may achieve 7 parts per million (ppm) integral non-linearity (INL) error, a 160 dB dynamic range (e.g., 100 femtoamps (fA) to 10 microamps (µA)), and/or may have a 197 dB Schreier figure of merit.

Figure 1A:
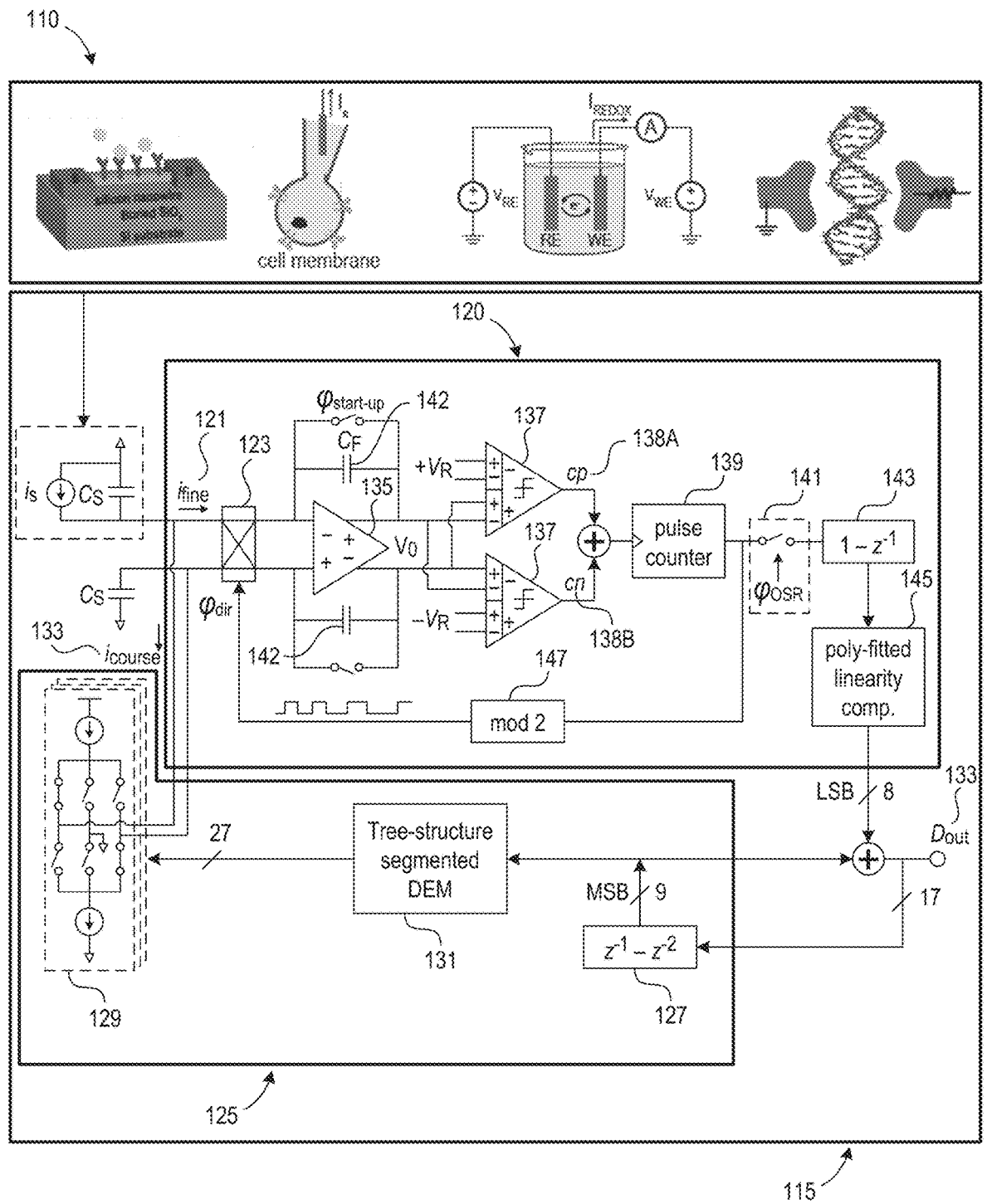
FIG. 1 depicts an example of a current measurement front-end, in accordance with some example embodiments.

FIG. 1A shows a block diagram of a wide dynamic range (DR) current-mode analog front-end (AFE) 115 and examples of biosensors 110. Analog front-end 115 includes predictive current-steering digital-to-analog converter (DAC) 125 (predictive DAC 125) and oversampling asynchronous hourglass ADC 120 (hourglass ADC 120). In some example embodiments, the predictive DAC 125 may have 9 bits of resolution, and/or the hourglass ADC 120 may have 8 bits of resolution. Unlike conventional $\Delta\Sigma$ modulators, the hourglass ADC 120 can tolerate a full-scale input current (10 µA). The predictive DAC 125 relaxes the power, linearity, and dynamic range requirements of the hourglass ADC.

To constrain the input range (e.g., $i_{fine} \leq \text{FullScale}/2^8$) to the hourglass ADC 120, a first-order digital predictor 127 may control a binary-weighted tri-state DAC 129 to generate an approximation of the input signal, $i_{coarse}$ 133, that is subtracted at the input from the input current is. The DAC 129 reduces the noise, area, and input capacitance. The input current, $i_{fine}$, to the hourglass ADC 120 may be expressed as:

$$i_{fine} = i_s - i_{coarse} \qquad \text{Equation 1}$$

where $i_s$ is the total input current and $i_{fine}$ and $i_{coarse}$ are described above. The DAC 129 may be implemented using a binary-weighted, tri-state topology to minimize the noise, area, and capacitance at the input node. The DAC 129 mismatch may be randomized using tree-structure, segmented dynamic element matching (DEM) 131. The residual current, $i_{fine}$ 121, may be quantized by the hourglass ADC 120 that may handle 2× the DAC unit current to tolerate prediction errors and remaining mismatch. The linearity of the hourglass ADC 120 may further be improved from <4 bits to >8 bits by a one-time offline calibration. A 17-bit digital code, $D_{out}$ 133, is obtained by combing the digital outputs of the predictor 127 and the hourglass ADC 120.

In conventional ADCs, either a single-stage ADC or a coarse-fine ADC architecture are used for high dynamic range (DR) applications. Instead of using a single-stage ADC or the coarse stage ADC with high DR and consuming more than 10× the power, the disclosed predictor provides an approximate input amplitude for the next oversampling cycle, so the hourglass ADC eliminates the need for a high precision and large DR coarse stage ADC. The digital predictor may control a DAC to determine the coarse residuals, $i_{fine}$, as the input of the hourglass ADC that represent <2-8 of the full DR with an oversampling ratio >5 Ix. In this way, the hourglass ADC can maintain >8 bits of linearity with a restricted input range.

The hourglass ADC is open-loop and asynchronous and includes a capacitive-feedback transimpedance amplifier (C-TIA) 135 and an hourglass switch 123 driven by the outputs of two continuous-time comparators 137. The hourglass switch 123 prevents the saturation of capacitor $C_F$ 142 by flipping the polarity of the input signal using the hourglass switch without needing a periodic reset, and improves the dynamic range, and reduces the input range to $i_{fine}$, a smaller input range than the input current. The hourglass switch is flipped asynchronously.

Figure 1B:
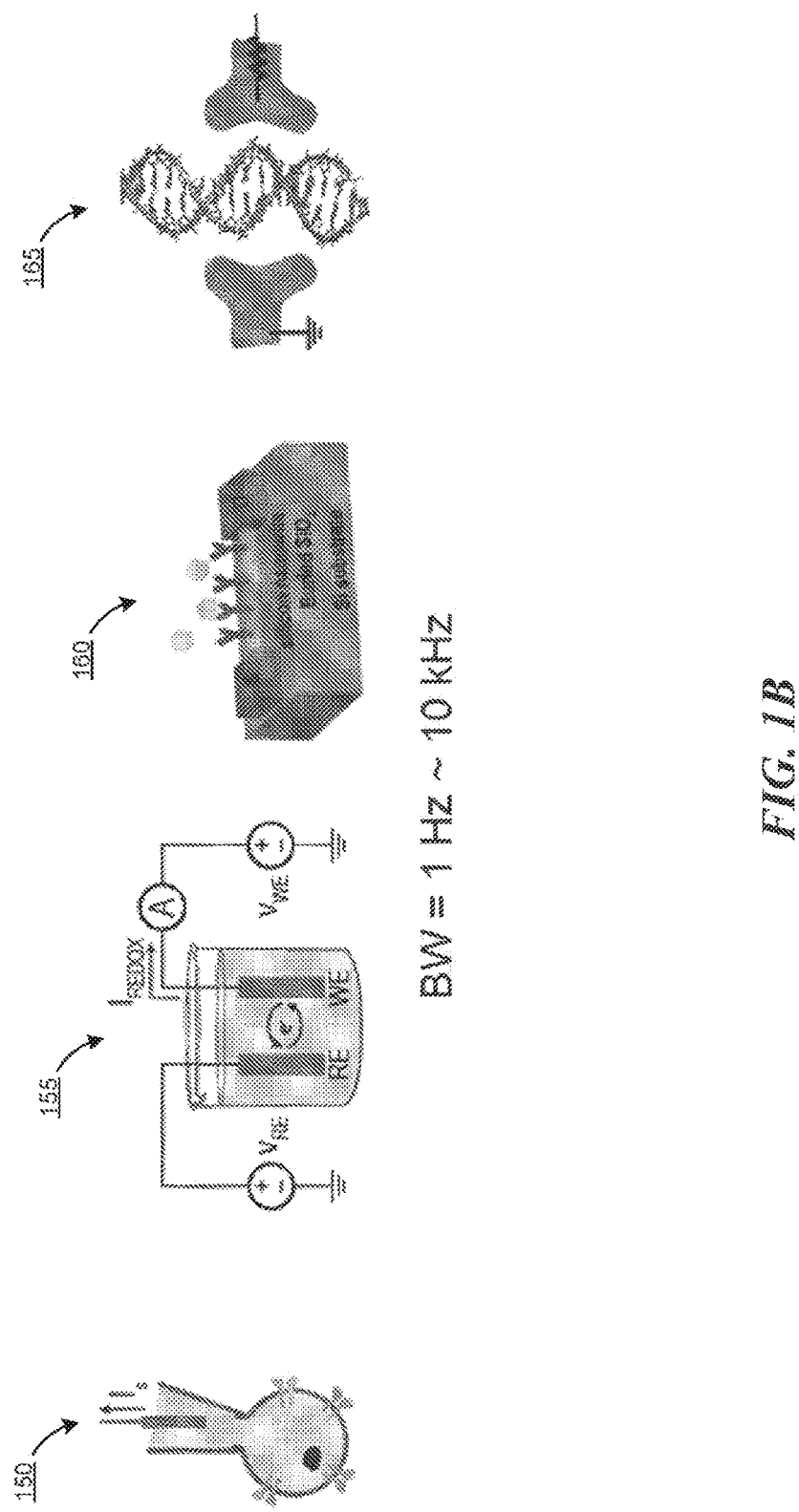

FIG. 1B shows some examples of biosensors that may be used with the disclosed analog front-end 115. Biosensors that generate current that can be measured using front-end 115 include patch-clamp 150, electrochemical cell 155, nanotube 160, nanopore 165, as well as other biosensors. Patch-clamp 150 includes one or more electrodes, cell membranes, and ion channels. Electrochemical cell 155 includes at least two electrodes submerged in a liquid in a container where an oxidation-reduction reaction generates a current that can be measured. Nanotube 160 includes target molecules that can bind with bioreceptors on a substrate. The bioreceptors may be attached to a silicon nanowire on silicon dioxide on a silicon substrate. Nanopore 165 may include electrodes and DNA, and other components. The range of current produced by some bioreceptors may be between about 1 picoamp (pA) and 1 microamp (uA). Some signals may be small with a large baseline value. For example, a 1 µA signal with a baseline current of 1 nA to 1 µA.

Figure 1C:
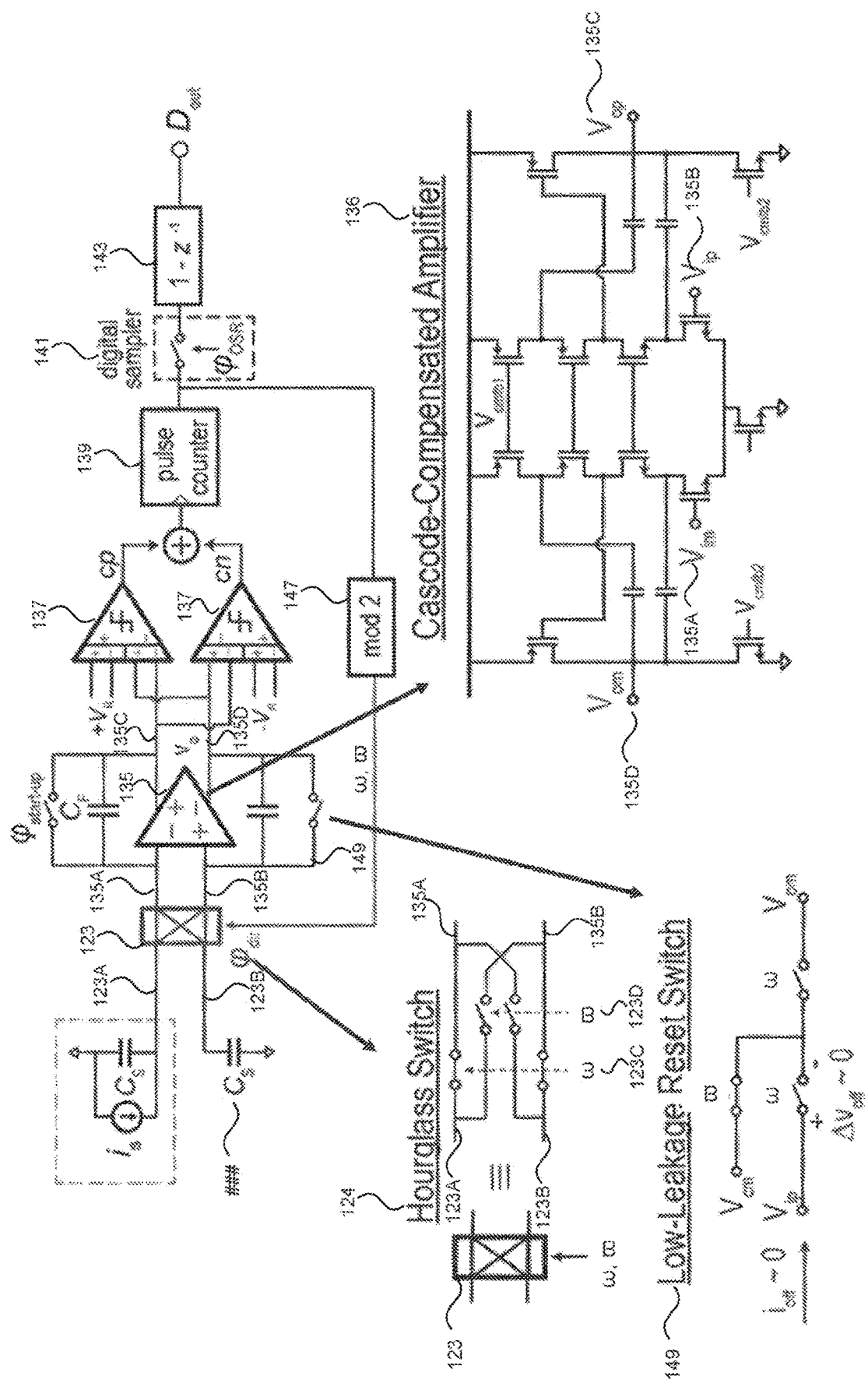

FIG. 1C depicts a diagram of an hourglass ADC and some example circuits. Hourglass switch 123 has inputs 123A and 123B and outputs 135A and 135B. The hourglass switch 123 is controlled by complementary inputs ω 123C and $\overline{\omega}$ 123D. For example, when ω 123C is a logic level high (H) and $\overline{\omega}$ 123D is a logic level low (L), input 123A is connected to output 135A and input 123B is connected to output 135B. In the opposite logic state, when ω 123C is L and $\overline{\omega}$ 123D is H, input 123A is connected to output 135B and input 123B is connected to output 135A. The foregoing is an example, and the logic states L and H may be reversed in the above. In this way, depending on ω 123C and $\overline{\omega}$ 123D, the inputs to transimpedance amplifier 135 may be reversed in polarity causing a charging of $C_F$ by the input or a discharging of $C_F$ by the input. Circuit 124 may perform as an hourglass switch 123 which may include four voltage or current controlled switches that are controlled by ω 123C and $\overline{\omega}$ 123D. The input to the hourglass switch may be modelled as a current source is in parallel with a source capacitance, $C_s$ as shown in FIG. 1C. $C_s$ may be up to about 5 picofarads or another capacitance value. $C_F$ may be about 0.1 picofarads or another capacitance. The input impedance into the amplifier 135 in the circuit of FIG. 1C has a low input impedance which is well suited for current source type inputs. The circuit in FIG. 1C can be reconfigured to be suited to voltage source inputs as well. The amplifier included in transimpedance amplifier 135 may include circuit 136 which may be referred to as a cascode compensated amplifier. A circuit corresponding to a switch 149 configured to discharge capacitor $C_F$, is shown at circuit 150 which may be controlled by ω 123C and $\overline{\omega}$ 123D or other signals. Other circuits included in the hourglass ADC include comparators 137, one comparator with threshold voltage set to $+V_R$ and another comparator with threshold voltage set to $-V_R$, pulse counter 139, digital sampler 141, digital transformation 143, and modulo 2 function 147. Digital sampler 141 and digital transformation 143 perform as a digital differentiator, reduces quantization noise, and provides first-order noise shaping.

Figure 2:
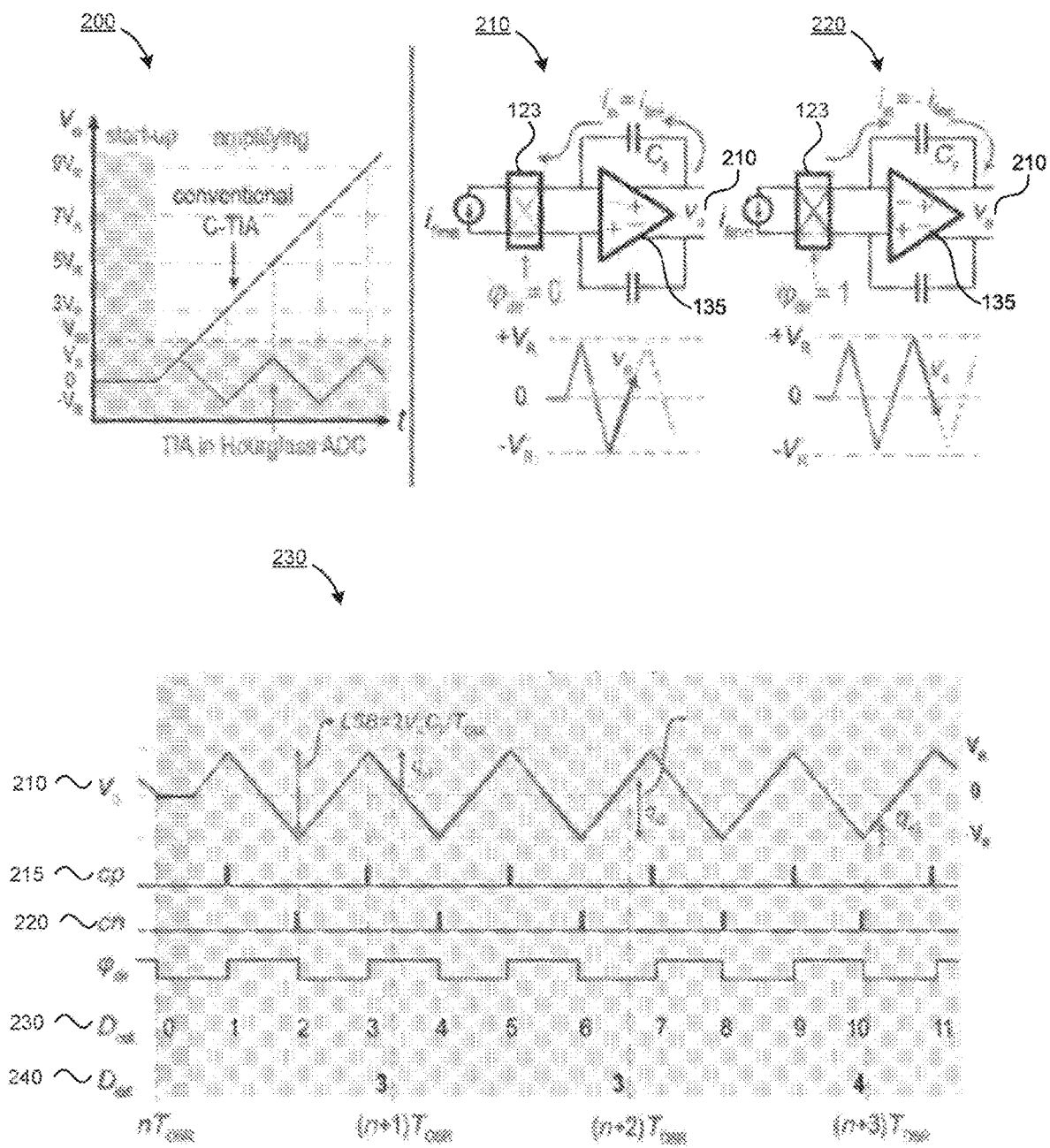
FIG. 2 depicts an example of an "hourglass" analog-to-digital converter (ADC), in accordance with some example embodiments.

FIG. 2 depicts circuits and voltage diagrams to further describe the functioning of the hourglass switch 123 and capacitive transimpedance amplifier (C-TIA) 135. The C-TIA 135 continuously integrates the input current and folds the output voltage within a predefined range of voltages, $\pm V_R$, by flipping the polarity of the input signal, $i_{fine}$, using the hourglass switch 123 resulting in a current to frequency conversion (I-to-F). In contrast to a periodically reset C-TIA, the asynchronous folding prevents the C-TIA from saturating by alternating between charging and discharging the feedback capacitor, $C_F$. Using the input current to charge and discharge $C_F$ may relieve the need for a DAC. Because the quantization error may be retained by not resetting $C_F$, the structure may provide first-order noise shaping.

FIG. 2 at 200 depicts an example of a plot of time vs. output voltage $v_o$ for a conventional C-TIA and the disclosed C-TIA with a constant input current. The output voltage of a conventional C-TIA grows continuously over time until a supply rail is reached. The output voltage of the C-TIA in the disclosed hourglass ADC reverses charging/discharging when the output voltage reached $+V_R$ or $-V_R$. For example, the output voltage increases as the C-TIA is charging capacitor $C_F$ as shown at 210. Once $+V_R$ is reached, the hourglass switch reverses the polarity of the input current and the C-TIA begins discharging as shown at 220. When the voltage reaches $+V_R$, comparator 137 triggers generating a pulse at $c_p$ 138A shown at 215. The pulse increments a counter with output at $D_{out}$ 230. The hourglass switch is then switched to reverse the polarity of the input current to cause $C_F$ to begin discharging. When the voltage reaches $-V_R$, comparator 137 triggers generating a pulse at $c_n$ 138B shown at 220. The pulse increments the counter shown at $D_{out}$ 230. The least significant bit of the counter corresponds to LSB=$2V_R C_F T_{OSR}$. At each sampling, no periodic reset is needed and a quantization error is stored. $D_{diff}$ at 240 is the digital result of differentiating the counter output $D_{out}$ 230.

Unlike an asynchronous ΔΣ with an asymmetric triangular waveform with a frequency inversely proportional to the input amplitude, the C-TIA 135 output is a symmetric triangular waveform with a fundamental frequency ($f_{dir}$=$i_s$/ $4V_R C_F$) which may be linearly proportional to the input amplitude. Due to the high oversampling ratio (OSR) and the DAC, the harmonic tones may be out-of-band and may be removed by a decimation filter. A counter may accumulate the number of comparator pulses, $c_p$ 138A and $c_n$ 138B shown in FIG. 1A. A digital representation of the signal may be obtained by sampling the output of the counter and digitally differentiating at the oversampling frequency, $f_{OSR}$. The hourglass structure enables wide dynamic range while providing the necessary low input impedance for current measurements.

Figure 3:
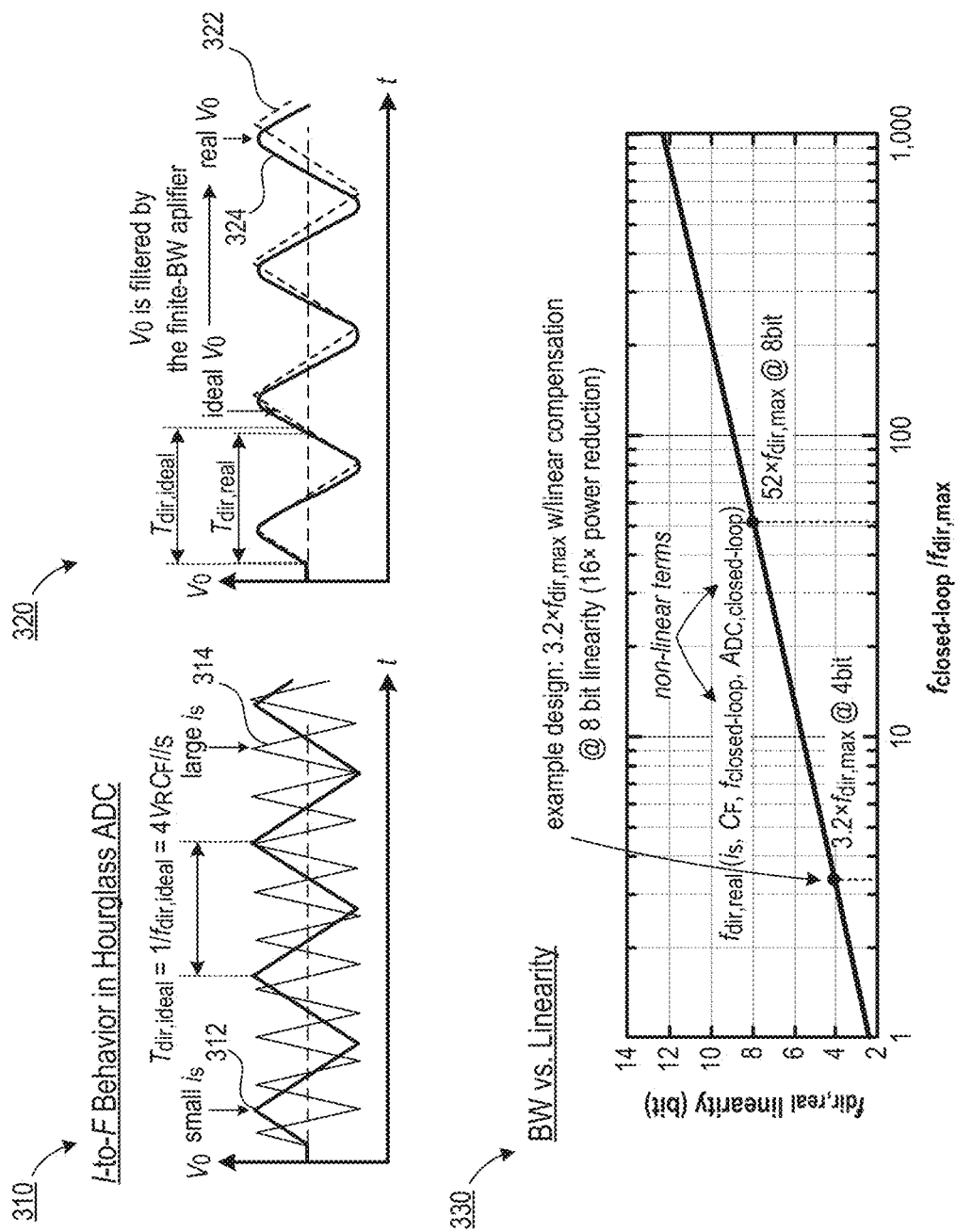
FIG. 3 depicts an example of a plot of I-to-F for an ADC, in accordance with some example embodiments.

The linearity of the hourglass ADC is due to, at least in part, to the C-TIA. FIG. 3 shows examples of plots showing a current-to-frequency (I-to-F) behavior of an hourglass ADC. At 310 is a plot of voltage vs. time showing the triangular output voltage of the C-TIA. For small input currents, the fundamental frequency of the triangular waveform 312 is lower than for higher currents shown at 314. At 320 is a plot of the triangular waveform 322 for an amplifier with unlimited bandwidth and at 324 for a more realistic amplifier with limited bandwidth. The limited bandwidth rounds the edges of the triangular waveform and delays the output as shown at 320. A triangular waveform has an infinite number of odd harmonics, but due to the filtering from the finite bandwidth of the amplifier in the disclosed C-TIA, the output waveform may be distorted. As the input current is increased, $f_{dir}$ linearly increases which may result in poorer linearity for a fixed bandwidth amplifier as shown at 330. By bounding the input current with the DAC, the number of harmonics, and thus the linearity of the hourglass ADC, can be ensured. For 8-bit linearity, the bandwidth of the amplifier may be approximately 52× larger, or more, than the maximum $f_{dir}$. Rather than implement such a wide bandwidth (>75 MHz) with a power-hungry amplifier, the linearity may be corrected digitally using an amplifier with a bandwidth only 3.2× larger than the maximum $f_{dir}$. Since the distortion can be expressed once the finite loop gain and bandwidth of the amplifier are known, the calibration routine may include using the DAC to sweep a subset of the I-to-F transfer function and fitting with a 5th order polynomial. This approach may result in 16× lower power compared to implementing a faster amplifier while ensuring >8 bits of linearity.

A two-stage differential amplifier may use dual cascode compensation to increase the unity-gain bandwidth with 2× smaller compensation capacitance than the equivalent Miller capacitor and reduce gain peaking beyond the unity-gain frequency. Some embodiments of the amplifier have >71° phase margin with $C_f$=100 fF and up to 5 pF of sensor capacitance. The DC gain (e.g., 99 dB) in conjunction with auto-zeroing may minimize the input offset voltage that modulates the sensor current during switching. A low-leakage reset switch may use three transmission gates to obtain an off-leakage of less than 100 fA. The hourglass switch may be implemented with transmission gates to minimize charge injection. The comparators may include a single stage preamplifier and a latch that may be auto-zeroed during the start-up phase to remove offset. The propagation delay of the comparator may be less than 5 ns to minimize dead-zone time and harmonic distortion caused by excess loop delay.

An analog front-end consistent with this disclosure may be implemented in a 0.18 μm CMOS process with a 1.8V supply and 0.5V and 1.3V reference voltages. Other semiconductor fabrication processes may also be used. It may be characterized with one of the differential inputs connected to a test source while the other is connected to a matched impedance network.

Figure 4:
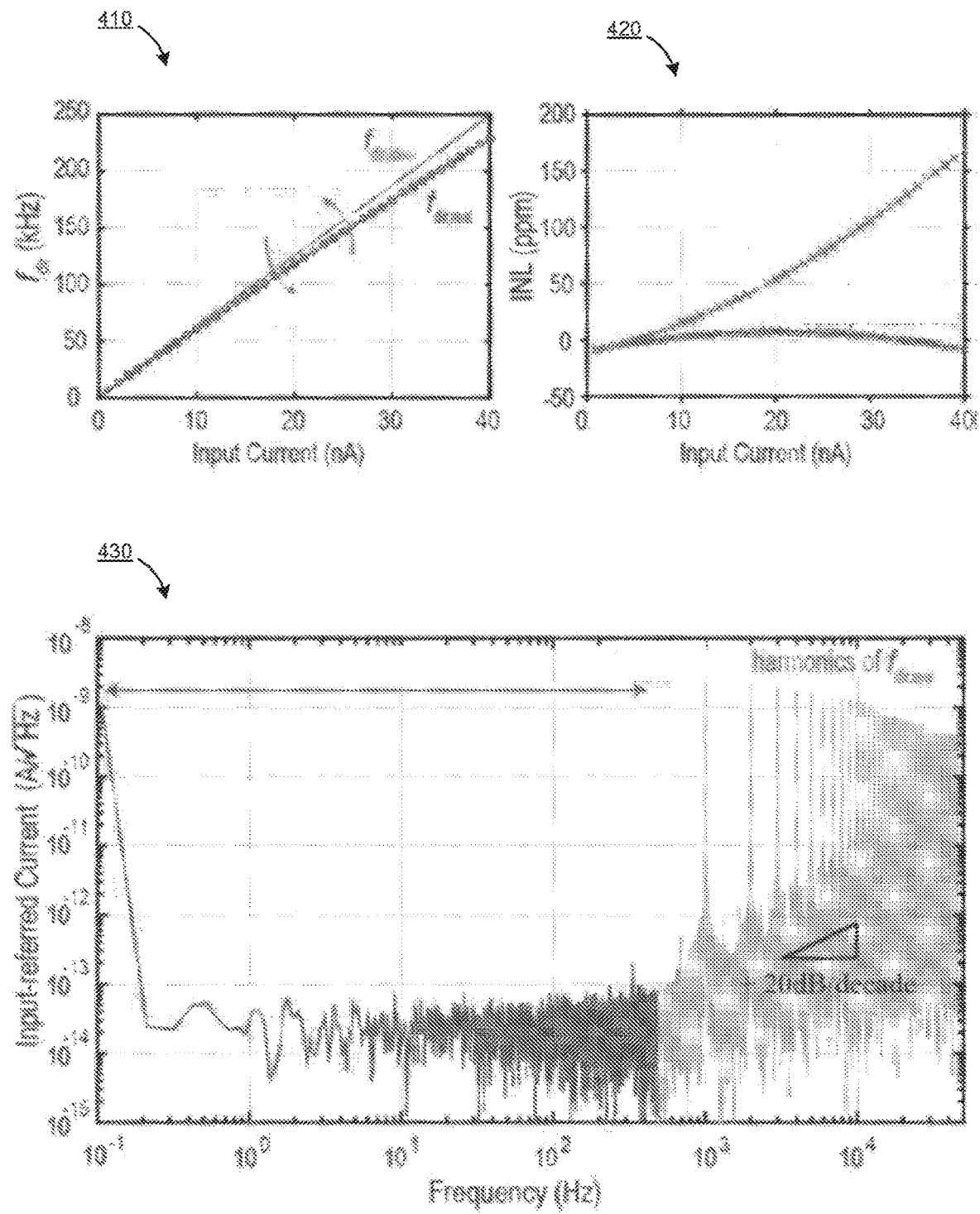
FIG. 4 depicts an example of performance characteristics of an hourglass ADC, in accordance with some example embodiments.

FIG. 4 depicts examples of plots at 410 and 420 of current-to-frequency (I-to-F) conversion for an example hourglass ADC. In some example embodiments, the hourglass ADC integral non-linearity may be improved using calibration (e.g., from >+50 ppm to <7 ppm). In an example embodiment, fitted parameters ($A_{DC,closed-loop}$=64 dB and $f_{closed-loop}$=1.5 MHz) closely match a result. FIG. 4 also shows at 430 a spectrum of the hourglass ADC with $f_{OSR}$=100 kHz illustrating a first order noise shaping. In some embodiments, for a conversion time of 400 ms (1.8 Hz BW), an input-referred noise of 79 $fA_{rms}$ may be measured.

Figure 5:
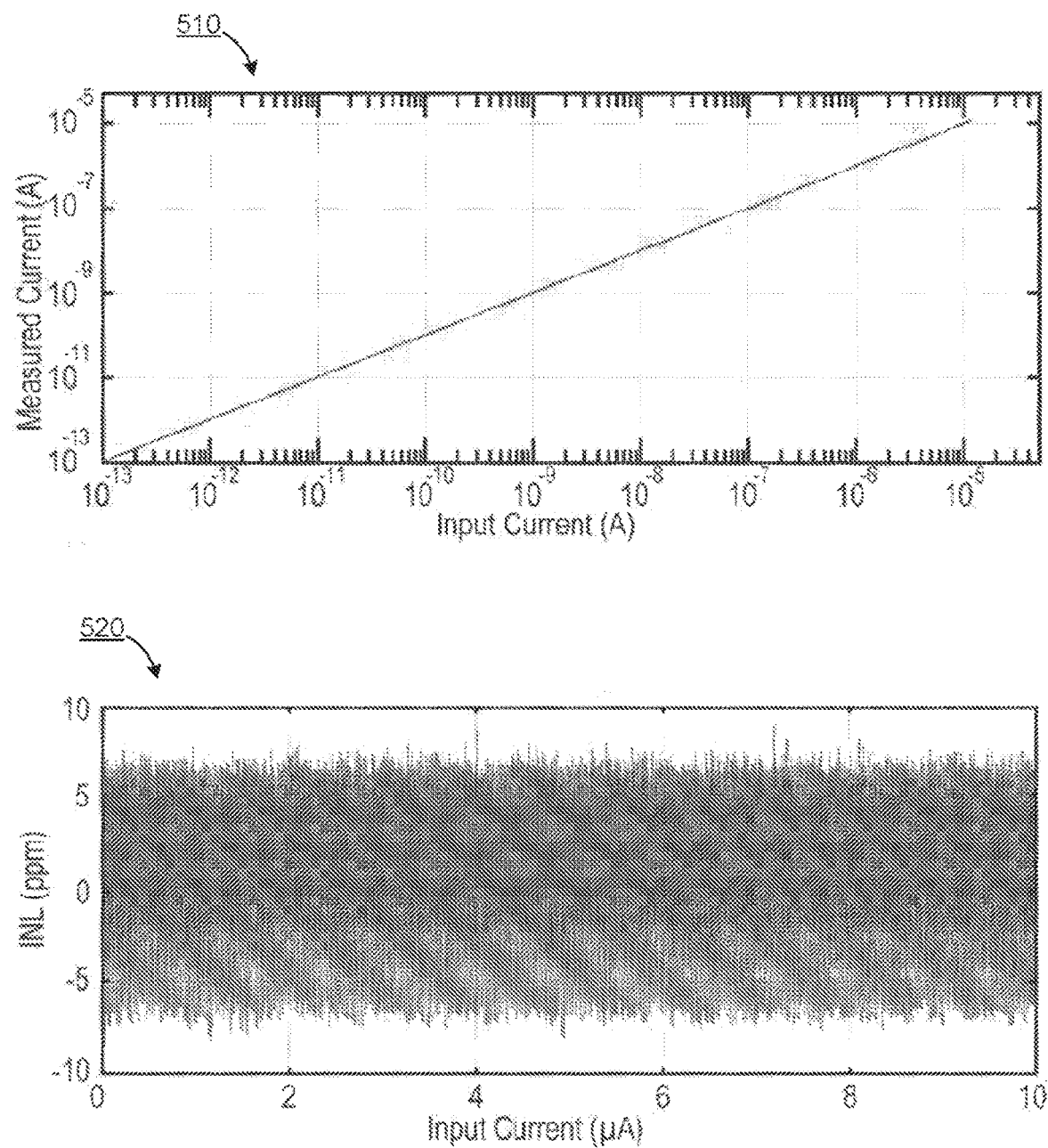
FIG. 5 depicts additional examples of performance characteristics of an hourglass ADC, in accordance with some example embodiments.

FIG. 5 shows an example at 510 of the full DR of an example analog front-end as the current is swept from 100 fA to 10 μA (160 dB). Shown at 520 is an example of a plot of INL vs. input current for an example embodiment showing a linearity of 7 ppm.

Figure 6:
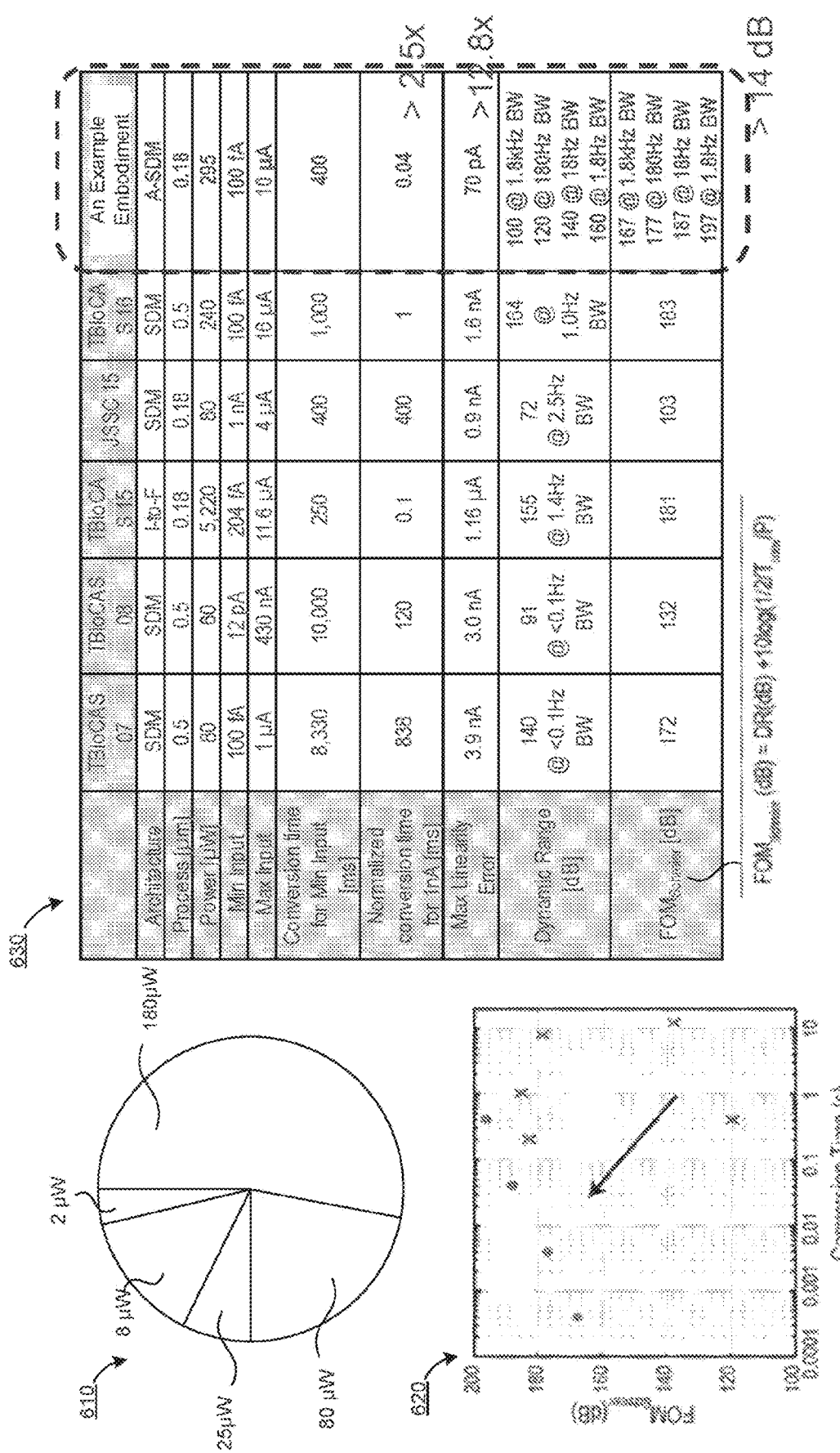
FIG. 6 depicts a performance summary of an hourglass ADC, in accordance with some example embodiments.

FIG. 6 depicts an example at 610 of a power consumption of an analog front-end. In the example at 610, the analog front-end consumes 295 μW. The amplifier consumes 180 μW. For flexibility, the digital logic including the predictor, DEM, and linearity correction may be implemented off-chip in a field programmable gate array (FPGA). For example, in this example the digital logic consumes 8 W. FIG. 6 at 620 summarizes the performance of an example analog front-end in comparison to other current-input ADCs with similar DRs and conversion times. Some example embodiments have a normalized conversion time of 0.04 ms for a 1nA current and a Schreier figure of merit of 197 dB shown at 630.

Figure 7:
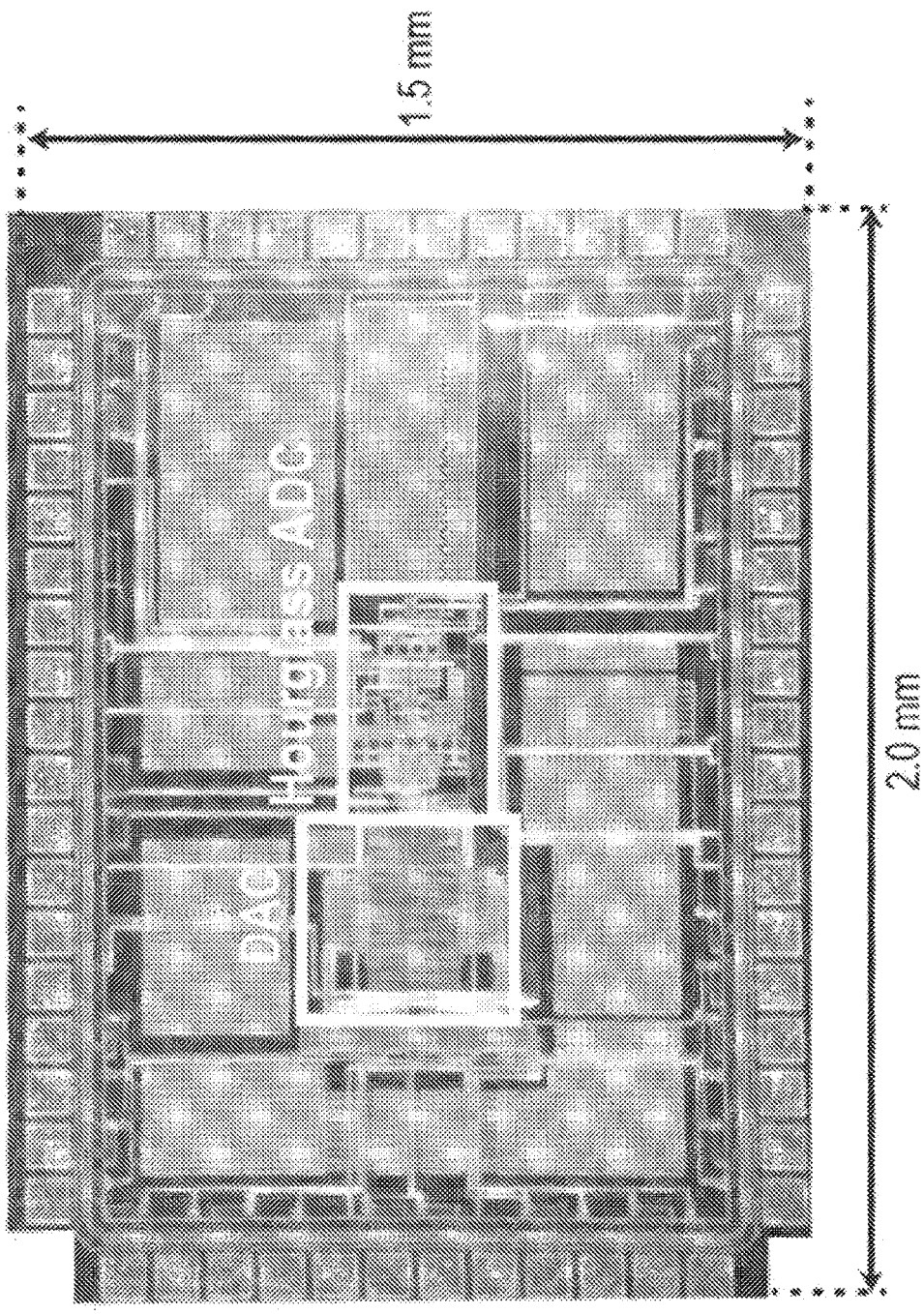
FIG. 7 depicts an example of a die micrograph, in accordance with some example embodiments.

FIG. 7 depicts a micrograph of a chip with a DAC and hourglass ADC. The example chip is 1.5×2.0 mm in size. The AFE occupies an area of 0.2 mm².

Figure 8:
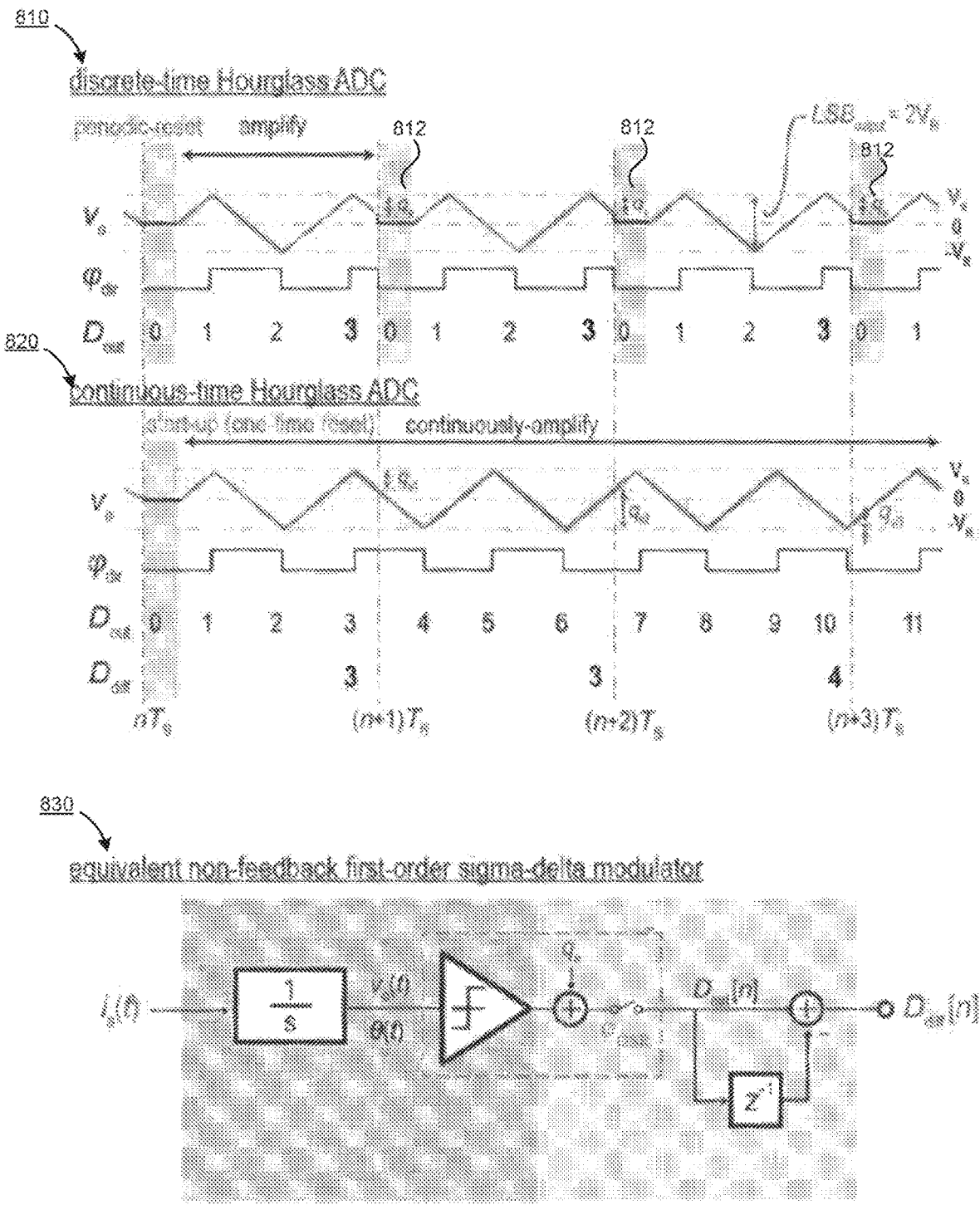
FIG. 8 depicts an example of a comparison between a periodic reset hourglass ADC and a continuously amplifying hourglass ADC, in accordance with some example embodiments.

FIG. 8 depicts a comparison of a periodic-reset discrete time hourglass ADC at 810 versus a continuously-amplifying hourglass ADC at 820. In the periodic reset example at 810, the C-TIA is reset periodically at 812. Due to a continuous amplification without periodic reset, the function of the hourglass ADC may be similar to a non-feedback first-order sigma-delta modulator shown at 830 when the asynchronous feedback loop serves as a quantizer and the digital differentiator provides first-order noise shaping behavior.

Figure 9:
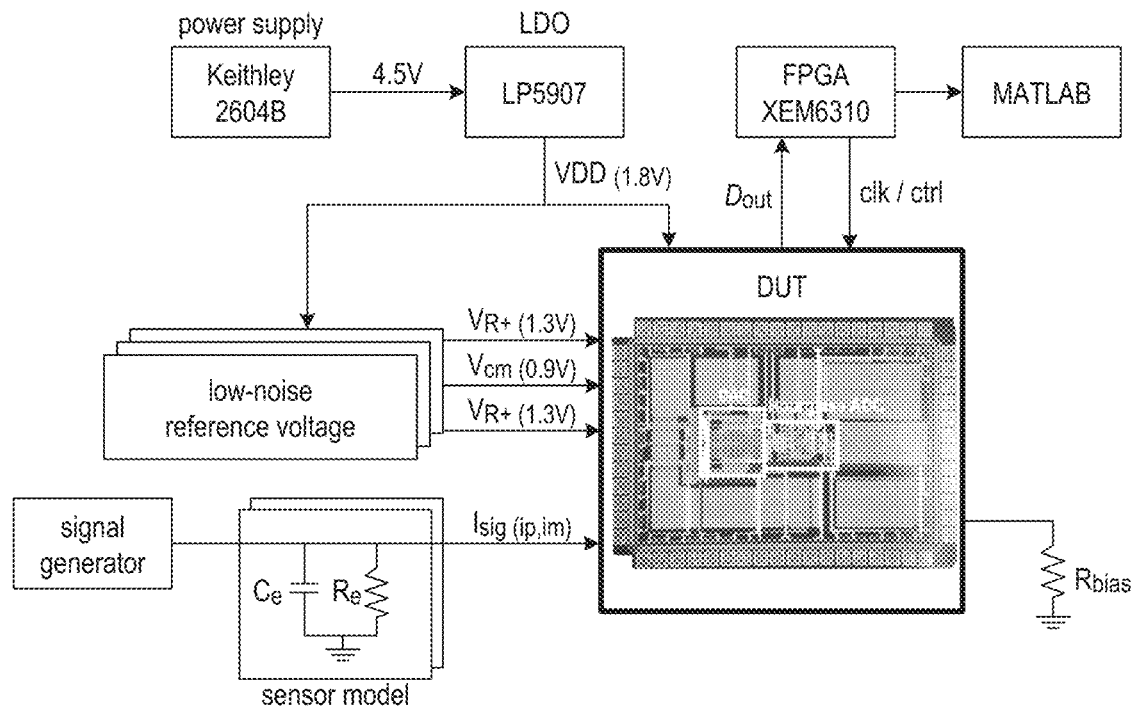
FIG. 9 depicts an example of a test set-up, a measurement environment, and a test printed circuit board (PCB), in accordance with some example embodiments.
Figure 9:
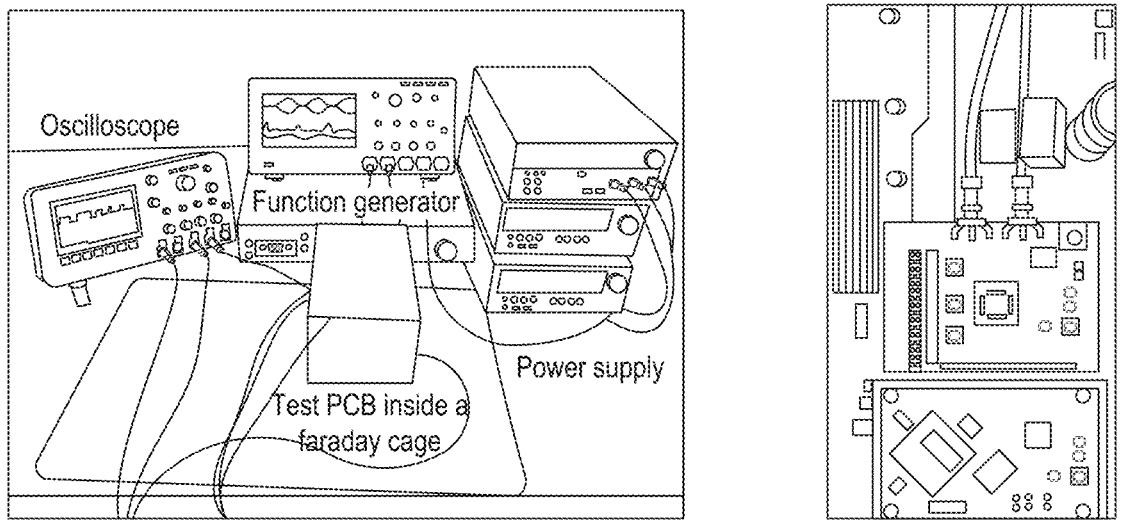

FIG. 9 depicts an example of a test setup for an hourglass ADC. Digital control signals may be provided by an FPGA, and the digital output of the hourglass ADC may be captured by the same FPGA and analyzed. The measurements may be performed inside a shielded faraday cage to minimize environmental interference.

Figure 10:
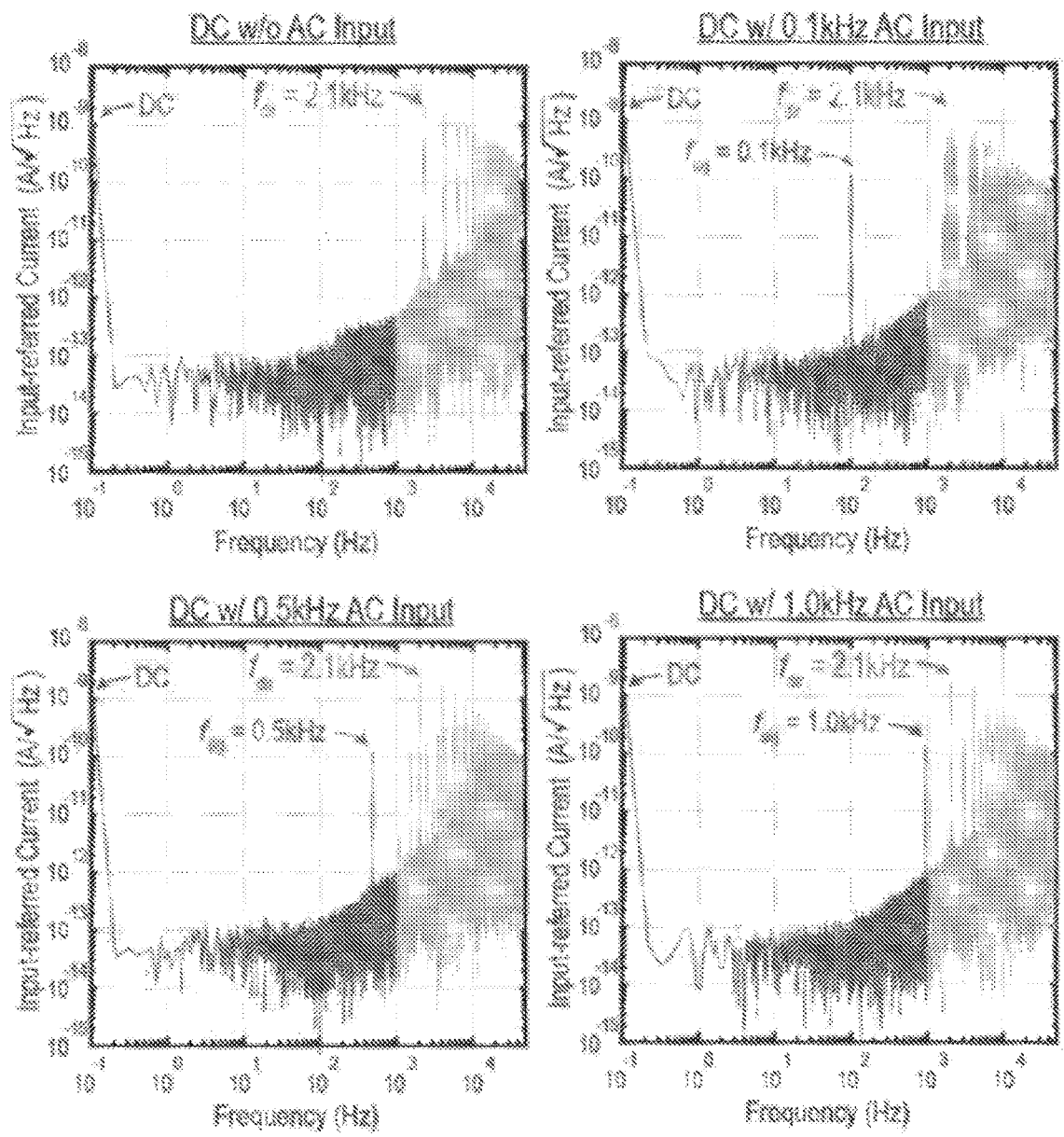
FIG. 10 depicts examples of plots of power spectral density, in accordance with some example embodiments.

FIG. 10 depicts examples of plots of power spectral density (PSD) of an input having 3.4 $nA_{DC}$ with and without 0.15 $nA_{AC}$ signals ($f_{sig}$=0.1, 0.5, and 1 kHz, respectively). The fundamental and harmonics of $f_{dir}$ are proportional to the amplitude of the DC, but independent to the amplitude and frequency of AC signals. This AC signal tone also shows up around the harmonic tones at $n×f_{dir}+f_{sig}$; for example, the 1.1 kHz tone exists on the bottom-right PSD due to the first harmonic of $f_{dir}$, i.e., $1×f_{dir}-f_{sig}$.

Figure 11:
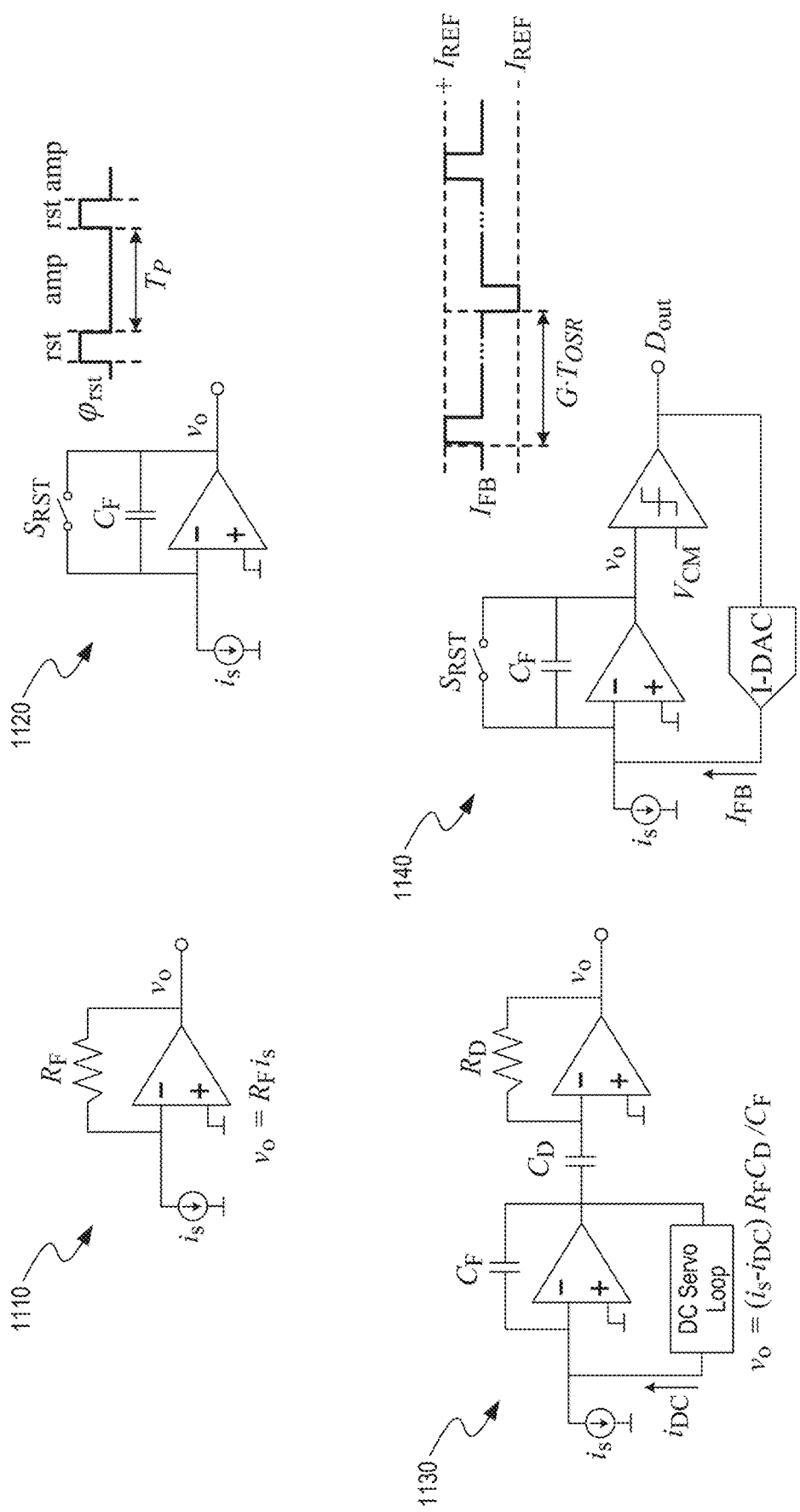
FIG. 11 depicts examples of various amplifier and comparator configurations.

FIG. 11 depicts examples of various amplifier and comparator configurations. At 1110 is a resistive transimpedance amplifier (R-TIA). R-TIA 1110 produces a voltage proportional to resistance R and input current is. This configuration exhibits high-noise and a low dynamic range (DR). At 1120 is a C-TIA. As shown at 1120, the C-TIA continues to integrate the input current until CF is saturated. This configuration has low noise, requires a periodic reset, and has a low dynamic range. At 1130 is a C-TIA with a DC servo loop. This configurations low-noise, can operate continuous-time, and has improved dynamic range over 1110 and 1120. At 1140 is a sigma-delta modulator with a pulse modulator. This configuration is low-noise, can operate continuous-time, has a high dynamic range but with slow conversion time. The subject matter disclosed in the above and FIGS. 1-10 overcome many of the limitations/disadvantages of the TIAs in FIG. 11.

FIG. 12 depicts a process at 1200, in accordance with some example embodiments. The process is a method of representing an analog voltage by a digital binary value. At 1210, the process includes integrating a fine input current at a transimpedance amplifiers. At 1220, the process includes selecting a polarity of the fine input current to integrate at the transimpedance amplifier. At 1230, the process includes, removing a coarse current from an input current leaving the fine current thereby reducing a dynamic range and improving the linearity of a circuit implementing the method.

At 1210, a fine input current is integrated by a transimpedance amplifier. The transimpedance amplifier has a non-inverting input and an inverting input. A first feedback capacitor is placed between an output of the transimpedance amplifier and the inverting input and a second feedback capacitor may be placed between the non-inverting input and another output. The output may be a non-inverting output and the other output may be an inventing output.

At 1220, a polarity of the fine input current is selected by switching between a first mode and a second mode. In the first mode, a first input is connected to a non-inverting input of the transimpedance and a second input is connected to an inverting input of the transimpedance amplifier. In the second mode, the first input is connected to the inverting input of the transimpedance amplifier and the second input is connected to the non-inverting input of the transimpedance amplifier. An hourglass switch performs the switching and is selected asynchronously to be in the first mode or the second mode to prevent the feedback capacitor from saturating.

At 1230, a coarse current is removed from an input current to the transimpedance amplifier leaving the fine current as the input to the transimpedance amplifier. By removing the coarse current removed from the input current, a range of the fine current is reduced thereby improving a linearity of a relationship between the analog input voltage and the digital binary value. The process may further include comparing, by a comparator, an output of the transimpedance amplifier to a reference voltage, wherein when the output exceeds the reference voltage the comparator generates a pulse, and wherein the pulse causes the hourglass switch to switch from the first mode to the second mode or the second mode to the first mode. The process may include counting pulses from the comparator including the pulse, wherein a count of the pulses is representative of the fine input current.

Although a few variations have been described in detail above, other modifications or additions are possible. In particular, further features and/or variations may be provided in addition to those set forth herein. Moreover, the example embodiments described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An analog-to-digital converter circuit comprising:
    a transimpedance amplifier including a feedback capacitor, wherein the transimpedance amplifier has a non-inverting input and an inverting input, and wherein the capacitor is electrically connected between the inverting or non-inverting input and an output of the transimpedance amplifier; and
    an hourglass switch electrically connected on a first side to a first input and a second input, and electrically connected on a second side to the non-inverting input and the inverting input, wherein a fine input current to the transimpedance amplifier is received at the first and second inputs, wherein in a first mode the hourglass switch electrically connects the first input to the non-inverting input and the second input to the inverting input, and wherein in a second mode, the hourglass switch electrically connects the second input to the non-inverting input and the first input to the inverting input.

2. The analog-to-digital converter circuit as in claim 1, further comprising:
    a linear digital-to-analog converter electrically connected to the first and second inputs, wherein the linear digital-to-analog converter generates a coarse current to remove from an input current leaving the fine input current as input current to the transimpedance amplifier at the first and second inputs.

3. The analog-to-digital converter circuit as in claim 2, further comprising:
    a comparator electrically connected to the output of the transimpedance amplifier and a reference voltage, wherein when the output exceeds the reference voltage the comparator generates a pulse, and wherein the pulse causes the hourglass switch to switch from the first mode to the second mode or the second mode to the first mode.

4. The analog-to-digital converter circuit as in claim 3, further comprising:
    a pulse counter electrically connected to the comparator to count pulses from the comparator including the pulse, wherein the pulse counter is representative of the fine input current.

5. The analog-to-digital converter circuit of claim 2, wherein the linear digital-to-analog converter comprises a first order predictor, a dynamic element matching circuit, and a binary-weighted digital-to-analog converter.

6. The analog-to-digital converter circuit as in claim 5, wherein the first order predictor estimates the input current for a next oversampling cycle and controls the binary-weighted digital-to-analog converter to generate the coarse current to be removed from the input current leaving the fine input current.

7. The analog-to-digital converter circuit as in any of claim 2, wherein the coarse current removed from the input current reduces a range of the fine current causing an improved linearity of the analog-to-digital converter circuit.

8. The analog-to-digital converter circuit as in claim 1, wherein the hourglass switch is a cross-point switch or a cross-bar switch.

9. The analog-to-digital converter circuit as in claim 1, further comprising:
    one or more sensors including one or more of a nanotube sensor, a patch-clamp sensor, an electro-chemical sensor, or a nanopore sensor, wherein the one or more sensors provide the input current.

10. The analog-to-digital converter circuit as in claim 1, wherein the hourglass switches asynchronously between the first mode or the second mode to prevent the feedback capacitor from saturating.

11. The analog-to-digital converter circuit as in claim 1, wherein the input current lies in a range between 100 femtoamps and 10 microamps.

12. The analog-to-digital converter circuit as in claim 1, wherein the hourglass switch and the linear analog to digital converter cause the analog-to-digital converter circuit to have a dynamic range of 160 dB or more.

13. The analog-to-digital converter circuit as in claim 1, wherein the hourglass switch and the linear analog to digital converter cause the analog-to-digital converter circuit to have a Schreier figure of merit equal to or greater than 197 dB.

14. A method of representing an analog voltage by a digital binary value comprising:

integrating, by a transimpedance amplifier including a feedback capacitor, a fine input current, wherein the transimpedance amplifier has a non-inverting input and an inverting input;

selecting a polarity of the fine input current by switching between a first mode, wherein a first input is connected to a non-inverting input to the transimpedance and a second input is connected to an inverting input to the transimpedance amplifier, or a second mode, wherein the first input is connected to the inverting input to the transimpedance and the second input is connected to the non-inverting input to the transimpedance amplifier, wherein an hourglass switch asynchronously selects the mode to be the first mode or the second mode to prevent the feedback capacitor from saturating; and removing a coarse current from an input current to the transimpedance amplifier, wherein the input current is equal to the fine input current added to the coarse current, wherein the coarse current removed from the input current reduces a range of the fine current and improves a linearity between the analog input voltage and the digital binary value.

15. The method of claim 14, further comprising:
comparing, by a comparator, an output of the transimpedance amplifier to a reference voltage, wherein when the output exceeds the reference voltage the comparator generates a pulse, and wherein the pulse causes the hourglass switch to switch from the first mode to the second mode or the second mode to the first mode.

16. The method of claim 15, further comprising:
counting pulses from the comparator including the pulse, wherein a count of the pulses is representative of the fine input current.

17. The method of claim 14, wherein the hourglass switch is a cross-point switch or a cross-bar switch.

18. The method of claim 14, wherein the coarse current is estimated by a linear digital-to-analog converter comprises a first order predictor, a dynamic element matching circuit, and a binary-weighted digital-to-analog converter.

19. The method of claim 18, wherein the first order predictor estimates the input current for a next oversampling cycle and controls the binary-weighted digital-to-analog converter to generate the coarse current to be removed from the input current leaving the fine current as the first and second inputs to the hourglass switch.

20. The method of claim 14, further comprising:
generating the input current by one or more sensors including one or more of a nanotube sensor, a patch-clamp sensor, an electro-chemical sensor, or a nanopore sensor, wherein the one or more sensors provide the input current.

21. The method of claim 14, wherein the input current lies in a range between 100 femtoamps and 10 microamps.

22. The method of claim 14, wherein a circuit performing the method has a dynamic range of 160 dB or more.

23. The method of claim 14, wherein a circuit performing the method has a Schreier figure of merit equal to or greater than 197 dB.

24. An analog-to-digital converter circuit comprising:
a transimpedance amplifier including a feedback capacitor, wherein the transimpedance amplifier has a non-inverting input and an inverting input, and wherein the capacitor is electrically connected between the inverting or non-inverting input and an output of the transimpedance amplifier; and an hourglass switch electrically connected on a first side to a first input and a second input, and electrically connected on a second side to the non-inverting input and the inverting input.

25. The analog-to-digital converter circuit as in claim 24, further comprising:
a linear digital-to-analog converter electrically connected to the first and second inputs, wherein an input current is received at the first and second inputs.

26. The analog-to-digital converter circuit as in claim 24, wherein in a first mode the hourglass switch electrically connects the first input to the non-inverting input and the second input to the inverting input, wherein in a second mode, the hourglass switch electrically connects the second input to the non-inverting input and the first input to the inverting input.

27. The analog-to-digital converter circuit as in claim 24, further comprising:
a comparator electrically connected to the output of the transimpedance amplifier and a reference voltage, wherein when the output exceeds the reference voltage the comparator causes the hourglass switch to switch from the first mode to the second mode or the second mode to the first mode.

28. The analog-to-digital converter circuit as in claim 27, further comprising:
a pulse counter to count pulses from the comparator including the pulse, wherein the pulse counter is representative of the fine input current.

* * * * *